United States Patent
Rothstock et al.

(10) Patent No.: US 10,278,753 B2
(45) Date of Patent: May 7, 2019

(54) BIOABSORBABLE OSTEOSYNTHESIS IMPLANT

(71) Applicant: BIOTRONIK AG, Buelach (CH)

(72) Inventors: Stephan Rothstock, Rostock (DE); Christoph Forkmann, Rostock (DE)

(73) Assignee: BIOTRONIK AG, Buelach (CH)

( * ) Notice: Subject to any disclaimer, the term of this patent is extended or adjusted under 35 U.S.C. 154(b) by 134 days.

(21) Appl. No.: 15/146,646

(22) Filed: May 4, 2016

(65) Prior Publication Data

US 2016/0331423 A1  Nov. 17, 2016

Related U.S. Application Data

(60) Provisional application No. 62/159,968, filed on May 12, 2015.

(51) Int. Cl.
*A61B 17/86* (2006.01)
*A61L 27/44* (2006.01)
*A61L 27/48* (2006.01)

(52) U.S. Cl.
CPC ........... *A61B 17/86* (2013.01); *A61L 27/44* (2013.01); *A61L 27/446* (2013.01); *A61L 27/48* (2013.01); *A61L 2430/02* (2013.01)

(58) Field of Classification Search
CPC ........ A61L 27/44; A61L 27/446; A61L 27/48; A61L 29/044; A61L 31/043; A61L 33/12; A61L 2300/604; A61L 2430/02; A61B 17/72; A61B 17/80; A61B 17/84; A61B 17/846; A61B 2017/00004; A61B 17/86–17/865; A61B 17/866; A61B 17/8685; A61B 17/869

USPC .................................................. 606/300–321
See application file for complete search history.

(56) References Cited

U.S. PATENT DOCUMENTS

| | | | | |
|---|---|---|---|---|
| 8,888,828 B2 * | 11/2014 | Belcheva | ........... | A61B 17/8645 606/300 |
| 2006/0021632 A1 | 2/2006 | Dobler et al. | | |
| 2006/0142772 A1 * | 6/2006 | Ralph | .................. | A61B 17/866 606/76 |
| 2008/0015578 A1 * | 1/2008 | Erickson | ............... | A61L 31/022 606/281 |
| 2008/0021465 A1 * | 1/2008 | Shadduck | .......... | A61B 17/7002 606/279 |
| 2011/0054629 A1 | 3/2011 | Seok et al. | | |
| 2014/0005731 A1 * | 1/2014 | Biedermann | ........ | A61B 17/686 606/328 |
| 2015/0105830 A1 * | 4/2015 | Biedermann | ...... | A61B 17/8685 606/317 |
| 2016/0022341 A1 * | 1/2016 | Agarwal | ............ | A61B 17/7032 606/308 |
| 2016/0331423 A1 * | 11/2016 | Rothstock | .......... | A61B 17/8033 |
| 2017/0156773 A1 * | 6/2017 | Beyar | .................. | A61B 17/866 |
| 2018/0325570 A1 * | 11/2018 | Kuntz | .................. | A61B 17/869 |

OTHER PUBLICATIONS

EP16165309.2 European Search Report dated Jun. 6, 2016.

* cited by examiner

*Primary Examiner* — Eric S Gibson
(74) *Attorney, Agent, or Firm* — Wagenknecht IP Law Group PC

(57) ABSTRACT

A bioabsorbable osteosynthesis implant, having a polymeric main body and at least one macroscopic reinforcement structure, which is integrated in the main body and is made of a biodegradable metal or a metal alloy.

12 Claims, 6 Drawing Sheets

BIOABSORBABLE OSTEOSYNTHESIS IMPLANT

CROSS REFERENCE TO RELATED APPLICATIONS

This application claims benefit of priority to U.S. provisional patent application No. 62/159,968, filed May 12, 2015, the content of which is herein incorporated by reference in its entirety.

TECHNICAL FIELD

The invention relates to a bioabsorbable osteosynthesis implant having a polymeric main body.

BACKGROUND

Osteosynthesis implants for the treatment of fractures, correction of malpositions, etc. made of biocompatible metals, such as titanium or titanium alloys or stainless steel, have long been known and used on a large scale. Permanent implants made of such materials remain in the body over the period of time for which they are required for stabilization of the fracture and can lead to complications and may require additional interventions for explantation. Furthermore, they permanently hold the fracture gap free from mechanical stresses and thus prevent a certain mechanical stimulation, which appears to be beneficial to the healing of the fracture.

On account of these and other disadvantages, efforts have long been made to develop optimal absorbable osteosynthesis implants. In particular, polymers have been taken into consideration as material for absorbable implants of this type. Polymers generally have a much lower rigidity than metal materials, whereby polymeric implants must have larger cross sections than metal implants having identical rigidity.

Degradable implants made of magnesium have currently proven to be successful for use as coronary stents. Compared to vascular implants, osteosynthesis implants have a much larger volume. High quantities of degradation products, particularly hydrogen, are thus produced during the degradation, which are problematic and cannot be absorbed quickly enough by the body.

WO 2010/034098 A1 discloses a biodegradable medical implant that can be embodied inter alia as an osteosynthesis implant and is formed from fine-grained metal and fine-grained polymeric material. The metal material can be embedded as small particles, fibers or flakes in a polymeric body.

US 2011/0054629 A1 describes a composite implant that has a porous structure which is filled microscopically with a biodegradable alloy or magnesium. The porous main structure can be produced from a metal, a ceramic or a polymer.

SUMMARY OF THE INVENTION

The object of the invention is to provide an improved absorbable osteosynthesis implant, which in particular does not allow degradation products to form more quickly than these can be removed from the body, has sufficient rigidity with minimal dimensions, and, during the course of fracture healing, transmits an increasingly greater load to the healing bone.

This object is achieved by a bioabsorbable osteosynthesis implant having the features of a polymeric main body and at least one macroscopic reinforcement structure as described herein, which is integrated in the main body and is made of a biodegradable metal or a biodegradable metal alloy Expedient developments of the invention are also disclosed herein.

In such an implant at least one macroscopic reinforcement structure made of a biodegradable metal or an appropriate metal alloy is integrated in a polymeric main body. The term "integrated" is also to include constructions in which the reinforcement structure protrudes partially from the polymeric main body.

By suitable arrangement of the reinforcement structure, tensile, flexural and torsional rigidity of the implant can be influenced independently of one another. Rigidity, degradation time and temporal course of the rigidity during the degradation can also be set differently in different regions of the implant. The implant can be completely bioabsorbable. The development of hydrogen during the magnesium degradation is much lower than is the case with an implant consisting completely of magnesium. Nevertheless, the higher rigidity of magnesium compared to polymers can be utilized.

In one embodiment of the invention the reinforcement structure includes a plurality of reinforcement struts in at least one region of the osteosynthesis implant. This may be a more or less central region of the implant, in which, with intended use, this central region is arranged opposite one or more fracture gaps of a bone structure to be treated. In currently expedient embodiments, the reinforcement struts in particular have a width/thickness in the range between 10 µm and 5 mm, especially between 50 µm and 2 mm, and even more especially between 100 µm and 1 mm.

Instead of reinforcement struts, a compact body made of the biodegradable metal or the metal alloy can also be embedded, or a plurality of reinforcement struts protruding into the surrounding polymeric main body can proceed from such a compact body.

In a further embodiment of the invention the implant is formed as a strip or elongate plate and has reinforcement struts running parallel to the longitudinal edges thereof. In currently expedient embodiments the strip or plate has a width/thickness in the range between 200 µm and 20 mm, especially between 500 µm and 10 mm, and even more especially between 1 and 5 mm.

Here, in accordance with one embodiment, at least some of the reinforcement struts running parallel to the longitudinal edges of the strip or plate extend over the entire length of the strip or plate. Additionally or alternatively, reinforcement struts can be provided that extend only over part of the length of the implant, in particular over the central region mentioned further above, which is arranged opposite one or more fracture gaps during use of the implant.

In another embodiment of the invention the implant is formed as a strip or elongate strip, but has at least a first and second group of reinforcement struts running at an incline to the longitudinal edges of the strip or plate, wherein the reinforcement struts of the first and second group cross each other in a region of the osteosynthesis implant. In one variant of this embodiment the implant has a plurality of first and second groups of reinforcement struts, which cross each other in each case in a crossover region.

In a further embodiment two aforementioned variants are combined in that reinforcement struts running at an incline to the longitudinal edges of the strip or plate are provided between parallel reinforcement struts running along the opposite edges, connecting these struts to one another functionally. The reinforcement struts running at an incline can be embodied here as part of the longitudinal extent of the edge-parallel reinforcement struts, but can also be provided at another height level of the polymeric main body as separate functional elements.

In a variant of the mentioned combination the reinforcement structure is formed as a lattice structure of reinforcement struts running parallel to the longitudinal edges of the strip or plate and running perpendicularly hereto. In a modification the lattice structure is not formed from perpendicularly oriented reinforcement struts, but from reinforcement struts oriented at an incline to one another, and for example has triangular or parallelogram-shaped reinforcement structure cells.

For other applications the proposed implant is formed as a bone screw, having at least one reinforcement strut running substantially parallel to the screw axis or wound around the screw axis, but preferably a plurality of reinforcement struts. The bone screw can be formed in particular with a diameter between 1 mm and 15 mm, especially between 2 mm and 10 mm.

For further applications the proposed implant is a medullary nail, having at least one reinforcement strut running substantially parallel to the nail axis, but preferably a plurality of reinforcement struts. The medullary nail can be formed currently in particular with a diameter between 500 μm and 10 mm and especially between 1 mm and 5 mm.

In a further embodiment the reinforcement structure is formed from magnesium or a magnesium alloy. Here, magnesium alloys containing rare earths, such as WE43, are particularly suitable.

In further material-related embodiments the polymeric main body includes a biopolymer, such as poly-L-lactate, polyglycolic acid, copolymers thereof or the like, and is in particular extruded, injection molded or also fiber-pressed. However, polymers such as polyethylene can also be used. Depending on the specific purpose and corresponding mechanical requirements, the polymer component may lie in the range between 50% and 99%, especially between 60% and 95%, and even more especially between 75% and 90% of the total mass of the main body.

In further embodiments the osteosynthesis implant in addition to the bioabsorbable main body having the integrated reinforcement structure also has a non-bioabsorbable component. This may also be integrated in the main body and where appropriate may protrude partially therefrom. Embodiments in which the non-bioabsorbable component is formed as an end portion or structural element of an end portion of a strip or plate or a bone screw or a medullary nail currently appear to be advantageous. Here, as a special variant, the bioabsorbable central part of such a composite implant may also consist exclusively of a biodegradable metal (without polymer component).

DESCRIPTION OF THE DRAWINGS

Advantages and expedient features of the invention will also emerge from the following description of exemplary embodiments on the basis of the figures, in which.

DETAILED DESCRIPTION

Figure 1:
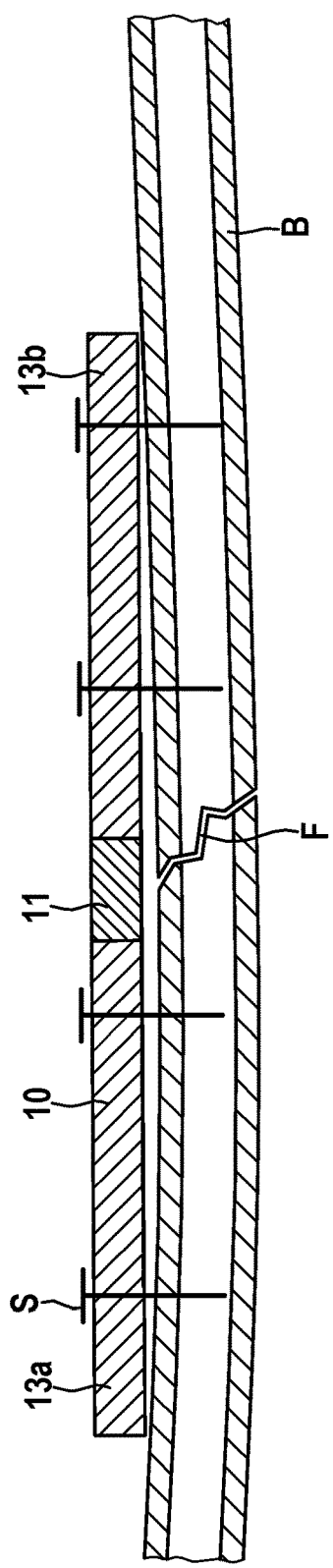
FIG. 1 shows a schematic side view of an embodiment of the invention in a use situation.

FIG. 1 schematically shows a fractured bone B with fracture gap F, to which a plate-like osteosynthesis implant 10 is secured by means of a number of bone screws S, the implant having a reinforcement structure 11 at a middle part, which is formed as a solid magnesium body and is positioned over the fracture gap F, and two end portions 13a, 13b formed from a biopolymer. The magnesium reinforcement structure 11 at the middle part can be degraded more quickly in the body than the end portions 13a, 13b consisting of the biopolymer, whereby an expediently controlled load transfer to the healing bone B during the course of healing of the fracture is made possible. The end portions 13a, 13b may also consist of a non-bioabsorbable material, for example a titanium alloy.

Figure 2:
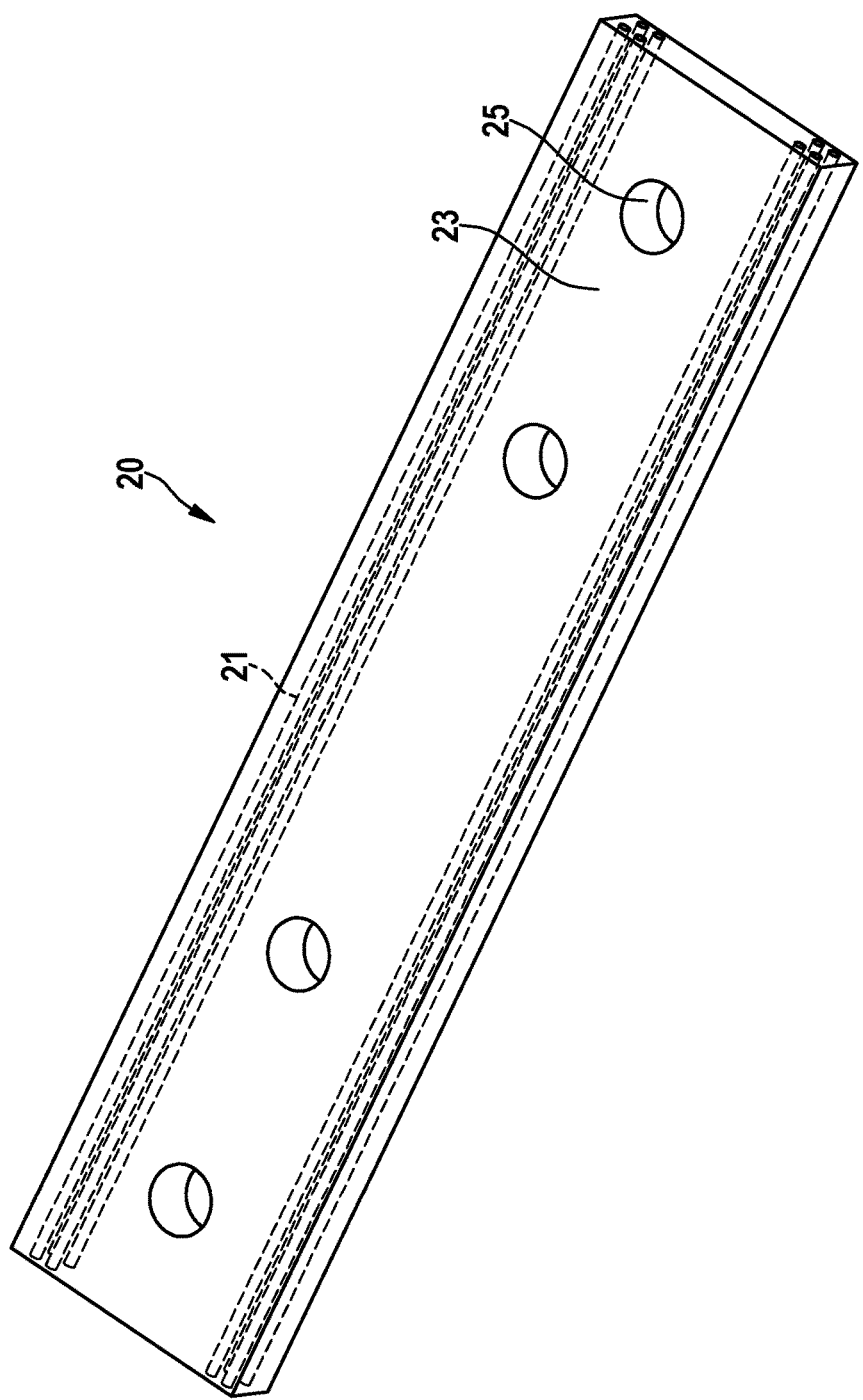
FIG. 2 shows a perspective illustration of a further exemplary embodiment.

FIG. 2 shows a perspective view of an osteosynthesis plate 20 having reinforcement structures embodied as reinforcement struts 21 (for example made of Mg or an Mg alloy) running parallel to the longitudinal edges, embedded in a polymeric main body 23 (for example made of poly-L-lactate). A number of cylindrical through-holes 25 for passing through bone screws are provided in the main body 23. In a group of a number of struts the reinforcement struts 21 are each integrated continuously from one end to the other end of the osteosynthesis plate 20. They are used to increase the flexural rigidity of the implant over the entire length thereof.

Figure 3:
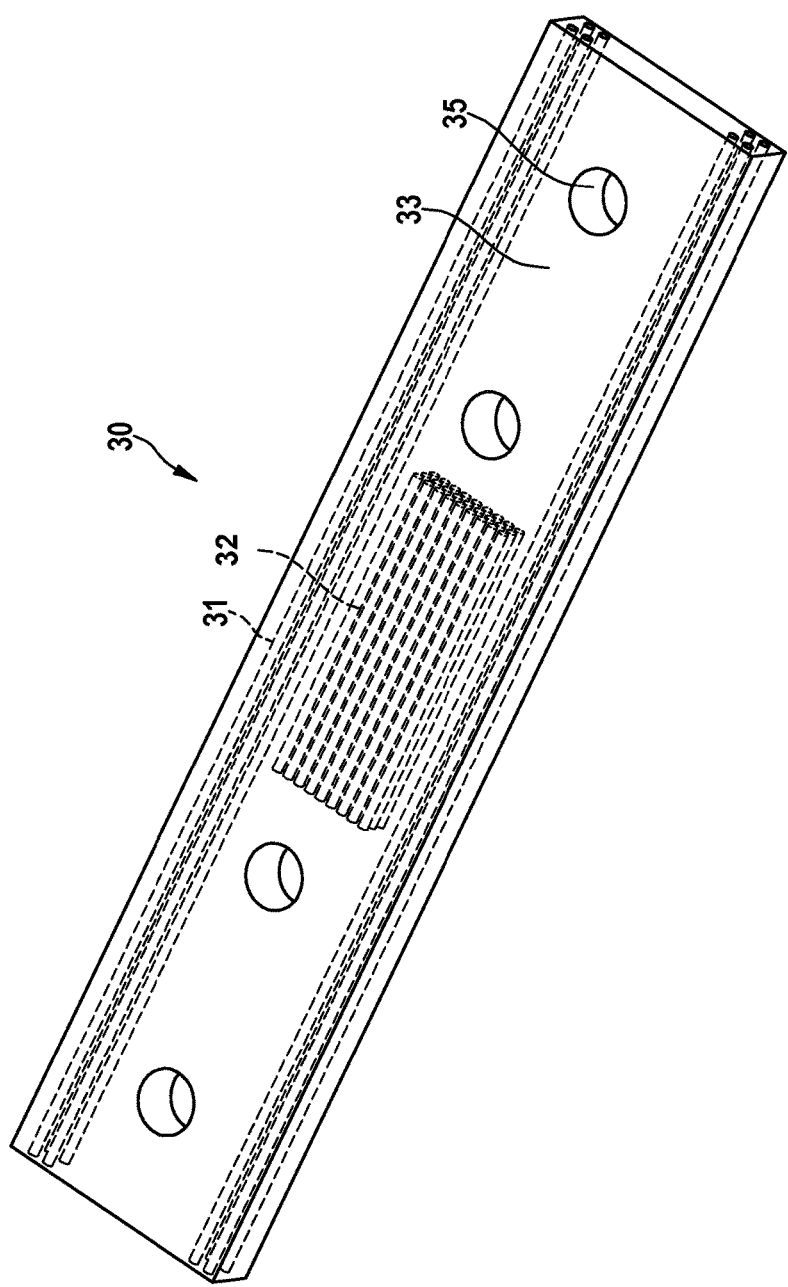
FIG. 3 shows a perspective illustration of a further exemplary embodiment.

FIG. 3 shows, as a modification of the previously mentioned embodiment, a further osteosynthesis plate 30, which besides continuous groups of reinforcement structures embodied as reinforcement struts 31, which run parallel to the longitudinal edges of the plate, also has an additional central reinforcement structure 32 in a main body 33, which additional reinforcement structure is likewise formed from the material of the reinforcement struts 31. Here, this additional reinforcement structure again may be a group of individual struts, but may also be a comb-like solid reinforcement part. This structure 32 increases additionally the flexural rigidity of the plate 30 in the middle region thereof.

Figure 4:
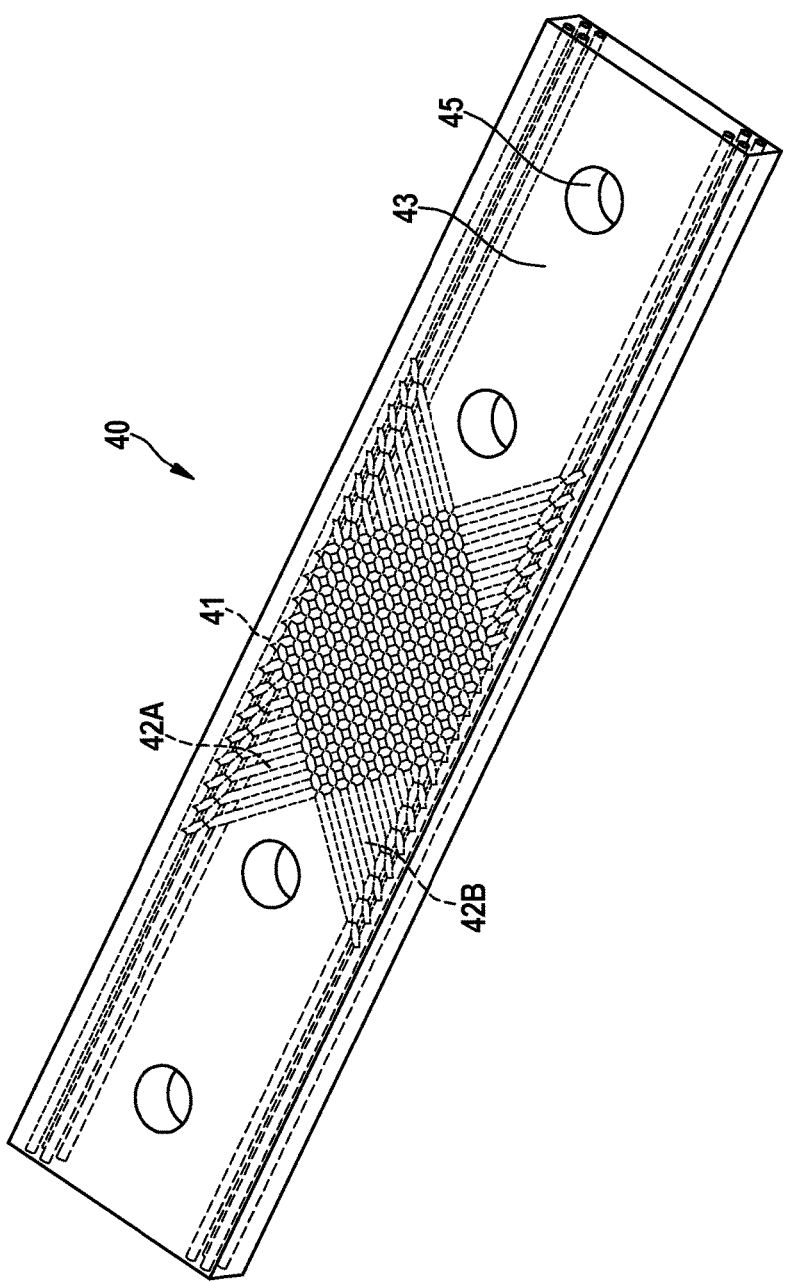
FIG. 4 shows a perspective illustration of a further exemplary embodiment.

FIG. 4 shows, as a further modification of the osteosynthesis plate from FIG. 2, a further osteosynthesis plate 40 having two groups of reinforcement structures embodied as reinforcement struts 41 running along the longitudinal edges. Here, an additional increase of the flexural rigidity in the middle region is provided by a first and second group 42A, 42B of reinforcement webs running at an incline to the longitudinal axes and crossing each other. The reinforcement strut groups 42A, 42B are arranged at different height level embedded in the polymeric main body 43. Also shown are number of cylindrical through-holes 45 for passing bone screws.

Figure 5:
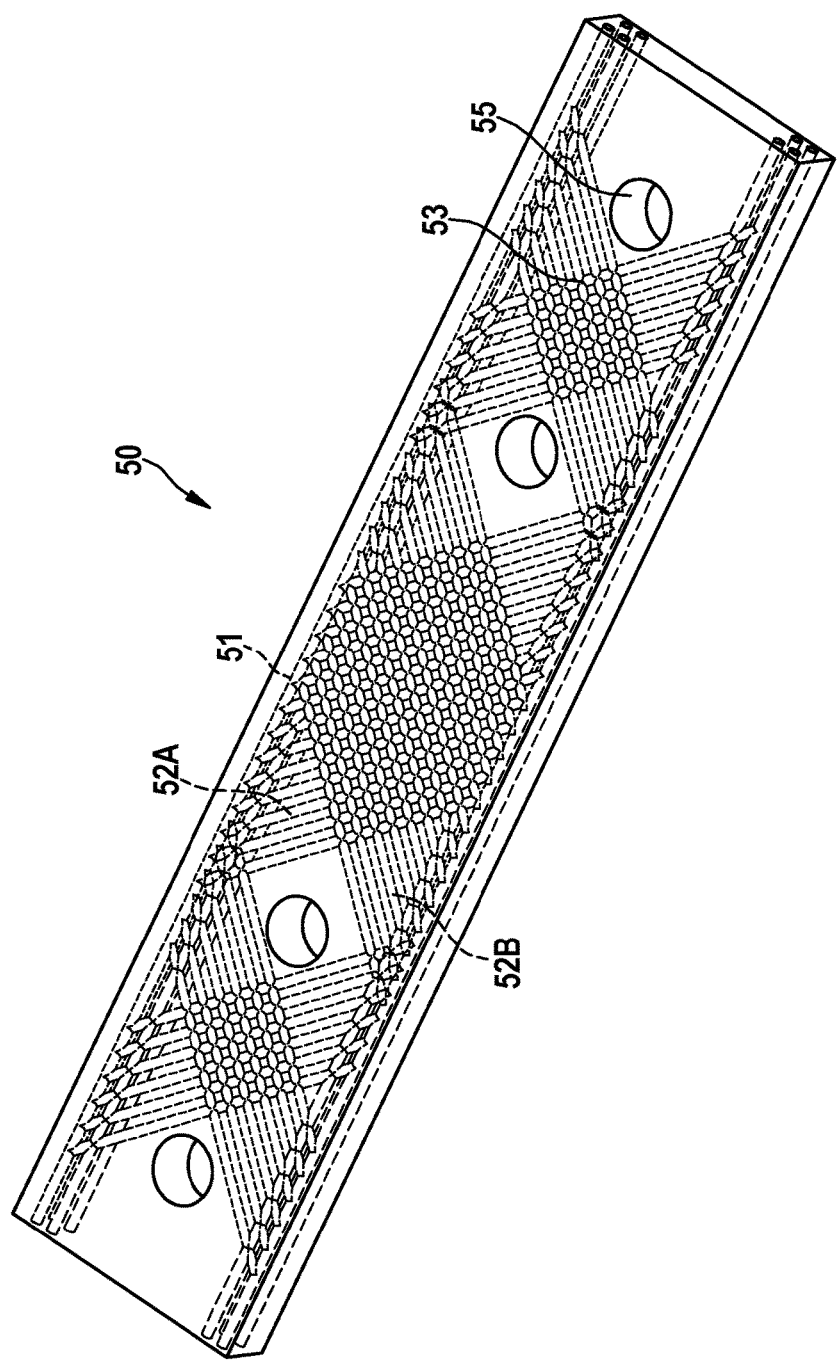
FIG. 5 shows a perspective illustration of a further exemplary embodiment.

FIG. 5 shows, as a modification of the aforementioned embodiment, an osteosynthesis plate 50, in which a plurality of first and second groups 52A, 52B of reinforcement structures embodied as reinforcement struts 51 each running at an incline to the longitudinal edges and crossing each other in the middle region of the polymeric main body 53 are arranged. An additional increase of the flexural rigidity is achieved in accordance with the plurality of additional reinforcement groups, moreover not only in the middle region of the implant, but practically over the entire length thereof. Also shown are number of cylindrical through-holes 55 for passing bone screws.

Figure 6:
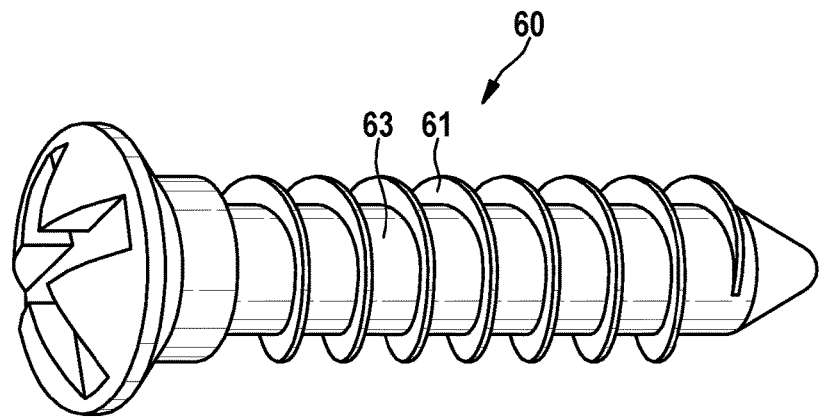
FIG. 6 shows a perspective illustration of a bone screw in one embodiment of the invention.

FIG. 6 shows a bone screw 60 having a polymeric screw body 63, in the outer periphery of which a reinforcement structure embodied as a reinforcement helix 61 made of a biodegradable metal alloy is added as screw thread. This reinforcement helix 61 is thus incorporated in part into the main body 63 and protrudes partially therefrom.

Figure 7:
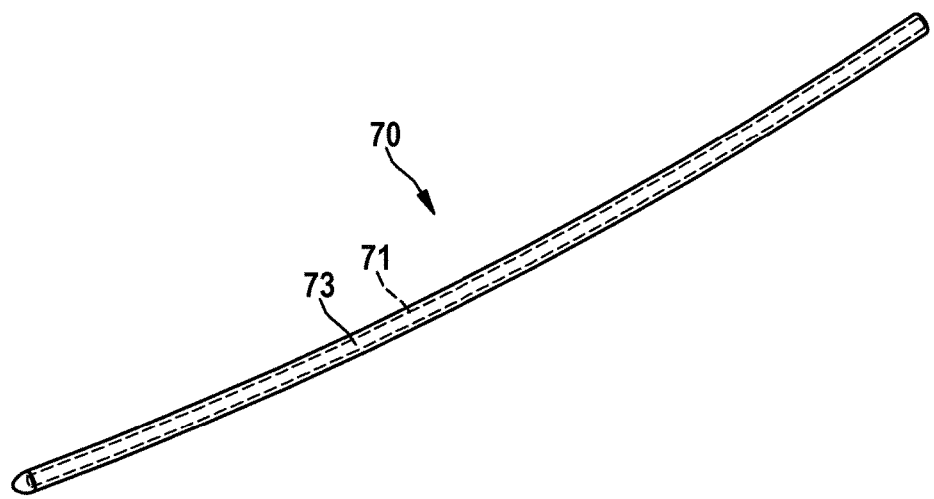
FIG. 7 shows a perspective illustration of a medullary nail in accordance with one embodiment of the invention.

FIG. 7 shows, as a further exemplary embodiment of the invention, a medullary nail 70, in which an individual reinforcement strut 71 (shown in a dashed manner in the figure) is embedded centrally in a polymeric main body 73.

In addition, the invention can also be embodied in a large number of modifications of the examples presented here and aspects of the invention highlighted further above.

It will be apparent to those skilled in the art that numerous modifications and variations of the described examples and embodiments are possible in light of the above teaching. The disclosed examples and embodiments are presented for purposes of illustration only. Other alternate embodiments may include some or all of the features disclosed herein. Therefore, is it the intent to cover all such modifications and alternate embodiments as may come within the true scope of this invention.

What is claimed is:

1. A bioabsorbable osteosynthesis implant, having a polymeric main body and macroscopic reinforcement structures, integrated in the main body and made of a biodegradable metal or a biodegradable metal alloy, wherein at least one of the reinforcement structures runs parallel to a longitudinal axis of the implant and at least another of the reinforcement structures runs inclined along the longitudinal axis.

2. The osteosynthesis implant of claim 1, formed as a bone screw having a diameter between 1 mm and 15 mm, wherein the longitudinal axis is parallel to a screw axis and the incline is wound around the screw axis.

3. The osteosynthesis implant of claim 1, wherein the reinforcement structure is formed from magnesium or a magnesium alloy.

4. The osteosynthesis implant of claim 1, wherein the polymeric main body comprises a biopolymer.

5. The osteosynthesis implant of claim 4, wherein the biopolymer is selected from the group consisting of a poly-L-lactate, polyglycolic acid, and copolymer thereof.

6. The osteosynthesis implant of claim 1, wherein the polymeric main body comprises a polymer component in a range between 50% and 99% of a total mass of the main body.

7. The osteosynthesis implant of claim 1, which has a non-bioabsorbable component.

8. A bioabsorbable osteosynthesis implant having a polymeric main body comprising a polymer component that is 50% to 99% of a total mass of the body and at least one macroscopic reinforcement structure, which is integrated in the main body and is made of a biodegradable metal or a biodegradable metal alloy, wherein the polymeric main body comprises a non-bioabsorbable component formed as an end portion or a structural element of an end portion of a bone screw.

9. The osteosynthesis implant of claim 8, wherein the at least one macroscopic reinforcement structure is oriented along an incline from a longitudinal axis.

10. The osteosynthesis implant of claim 8, wherein the at least one macroscopic reinforcement structure is helically oriented around a longitudinal axis.

11. A bone screw comprising a polymeric main body and a macroscopic reinforcement structure comprising a biodegradable metal or biodegradable metal alloy integrated in the main body, wherein the reinforcement structure partially protrudes in a helical orientation from the main body to form an outer thread.

12. The bone screw of claim 11, further comprising another macroscopic reinforcement structure embedded in the main body and aligned parallel to a longitudinal axis of the screw.

* * * * *